(12) United States Patent
Mueller et al.

(10) Patent No.: US 11,304,732 B2
(45) Date of Patent: Apr. 19, 2022

(54) POLYAXIAL BONE SCREW

(71) Applicant: CoreLink, LLC, St. Louis, MO (US)

(72) Inventors: Mike Mueller, Fenton, MO (US); Adam MacMillan, Fenton, MO (US)

(73) Assignee: CORELINK, LLC, St. Louis, MO (US)

( * ) Notice: Subject to any disclaimer, the term of this patent is extended or adjusted under 35 U.S.C. 154(b) by 0 days.

(21) Appl. No.: 17/030,996

(22) Filed: Sep. 24, 2020

(65) Prior Publication Data

US 2021/0085373 A1 Mar. 25, 2021

Related U.S. Application Data

(60) Provisional application No. 62/905,119, filed on Sep. 24, 2019.

(51) Int. Cl.
*A61B 17/70* (2006.01)
*A61B 17/00* (2006.01)

(52) U.S. Cl.
CPC ........ *A61B 17/7034* (2013.01); *A61B 17/704* (2013.01); *A61B 17/7082* (2013.01); *A61B 2017/00367* (2013.01); *A61B 2017/00867* (2013.01)

(58) Field of Classification Search
CPC ............ A61B 17/7032; A61B 17/7034; A61B 17/7035; A61B 17/704; A61B 17/86; A61B 17/8605
USPC ................................................. 606/265–269
See application file for complete search history.

(56) References Cited

U.S. PATENT DOCUMENTS

| | | | |
|---|---|---|---|
| 8,197,518 B2* | 6/2012 | Hammill, Sr. | A61B 17/7037 606/269 |
| 8,388,660 B1* | 3/2013 | Abdou | A61B 17/8685 606/267 |
| 10,076,362 B2* | 9/2018 | Biedermann | A61B 17/7037 |
| 2012/0185003 A1 | 7/2012 | Biedermann et al. | |
| 2014/0012337 A1 | 6/2014 | Biedermann et al. | |
| 2015/0142059 A1 | 5/2015 | Biedermann et al. | |
| 2018/0014863 A1* | 1/2018 | Biester | A61B 17/8615 |
| 2019/0015144 A1 | 1/2019 | Biedermann et al. | |
| 2019/0150990 A1 | 5/2019 | Jackson et al. | |

OTHER PUBLICATIONS

International Search Report & Written Opinion, PCT/US2020/052475, dated Jan. 6, 2021, pp. 10.

* cited by examiner

*Primary Examiner* — Eduardo C Robert
*Assistant Examiner* — Christina NegrelliRodriguez
(74) *Attorney, Agent, or Firm* — Stinson LLP

(57) ABSTRACT

A bone screw assembly includes a fastener including a shaft and a head disposed on the shaft. The fastener is configured to be anchored within a subject's bone. A receiving assembly is configured to be movably mounted on the head of the fastener. The receiving assembly includes a receiver disposable around at least a portion of the head of the fastener and defining a channel for receiving a rod member therein. A retaining ring is disposed within the receiver for holding the head of the fastener in the receiver. An insert is disposed in the receiver above the retaining ring. A saddle is disposed in the receiver above the insert. The saddle defines a cradle for seating the rod member in the receiver.

15 Claims, 21 Drawing Sheets

POLYAXIAL BONE SCREW

CROSS-REFERENCE TO RELATED APPLICATION

This application claims priority to U.S. Provisional Patent Application Ser. No. 62/905,119, filed Sep. 24, 2019, which is hereby incorporated by reference in its entirety.

FIELD OF THE DISCLOSURE

The present disclosure is directed to bone screws, and more particularly to polyaxial bone screws for use in spinal surgery.

BACKGROUND OF THE DISCLOSURE

Bone screws may be used to anchor implants to vertebrae along the spinal column for the purpose of stabilizing and/or adjusting spinal alignment. Spinal fusion surgery may require placement of bone screws through small incisions with limited visibility for connecting vertebrae to rods. Due to the difficulty in placing bone screw in such procedures, polyaxial screw are often used. Polyaxial screw assemblies allow for rotational and pivotable movement of a receiver about the head of a fastener until a desired position of the receiver is achieved. A rod or other connecting member may then be inserted into a channel of the receiver and secured in place by a locking member engaged with the receiver.

SUMMARY OF THE DISCLOSURE

In one aspect, a bone screw assembly generally comprises a fastener comprising a shaft and a head disposed on the shaft. The fastener is configured to be anchored within a subject's bone. A receiving assembly is configured to be movably mounted on the head of the fastener. The receiving assembly comprises a receiver disposable around at least a portion of the head of the fastener and defining a channel for receiving a rod member therein. A retaining ring is disposed within the receiver for holding the head of the fastener in the receiver. An insert is disposed in the receiver above the retaining ring. A saddle is disposed in the receiver above the insert. The saddle defines a cradle for seating the rod member in the receiver.

In another aspect, a receiving assembly for a bone screw generally comprises a receiver configured to be movably mounted on a head of the bone screw. The receiver defines a channel for receiving a rod member therein. A retaining ring is disposed within the receiver for holding the head of the bone screw in the receiver. An insert is disposed in the receiver above the retaining ring. A saddle is disposed in the receiver above the insert. The saddle defines a cradle for seating the rod member in the receiver.

In yet another aspect, a receiving assembly for a bone screw generally comprises a receiver configured to be movably mounted on a head of the bone screw. The receiver defines a channel for receiving a rod member therein. A continuous retaining ring is disposed within the receiver for holding the head of the bone screw in the receiver. The continuous retaining ring is configured to expand a receiving area of the retaining ring to permit at least a portion of the head of the bone screw to be inserted through the retaining ring.

BRIEF DESCRIPTION OF THE DRAWINGS

Corresponding reference characters indicate corresponding parts throughout the drawings.

DETAILED DESCRIPTION OF THE DISCLOSURE

Figure 1:
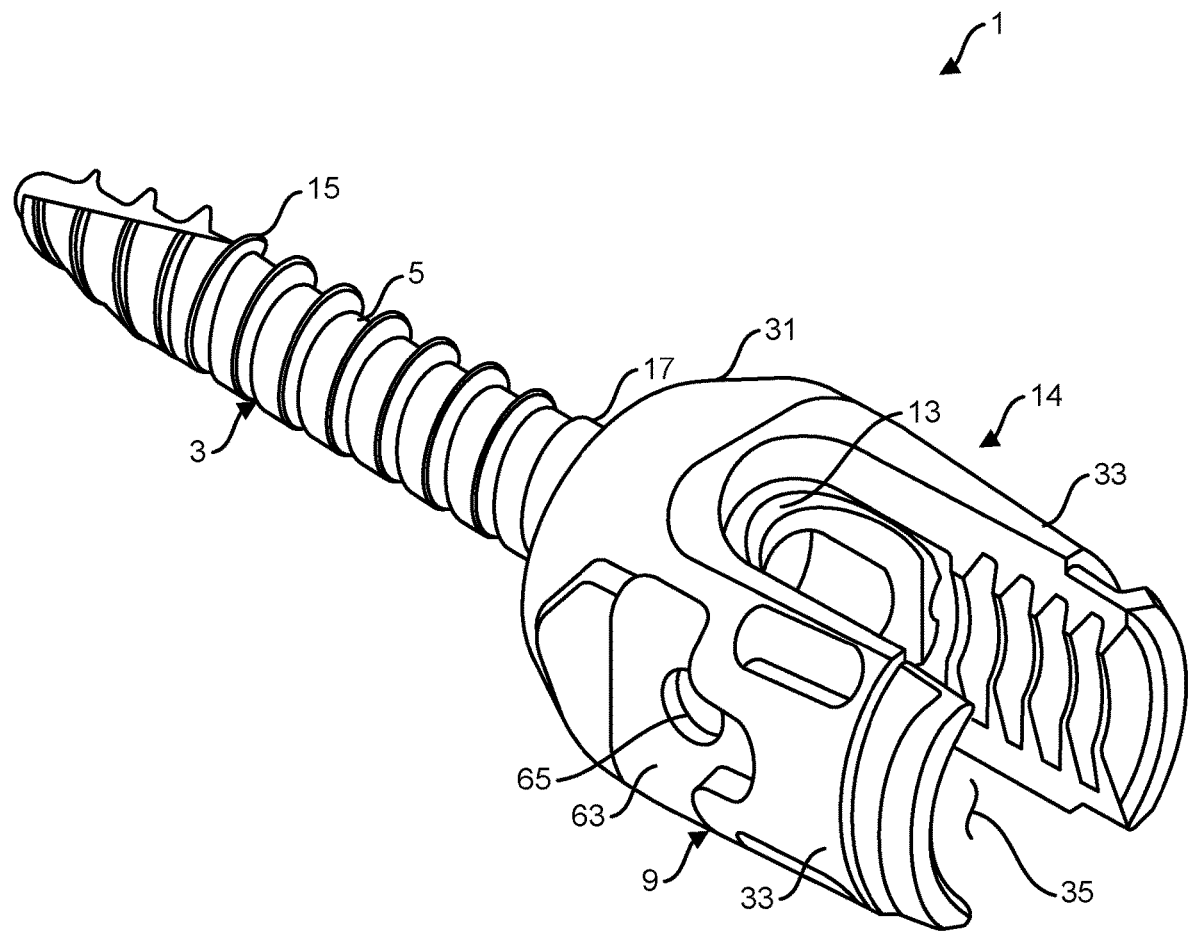
FIG. 1 is a perspective of one embodiment of a bone screw assembly constructed according to the teachings of the present disclosure.
Figure 2:
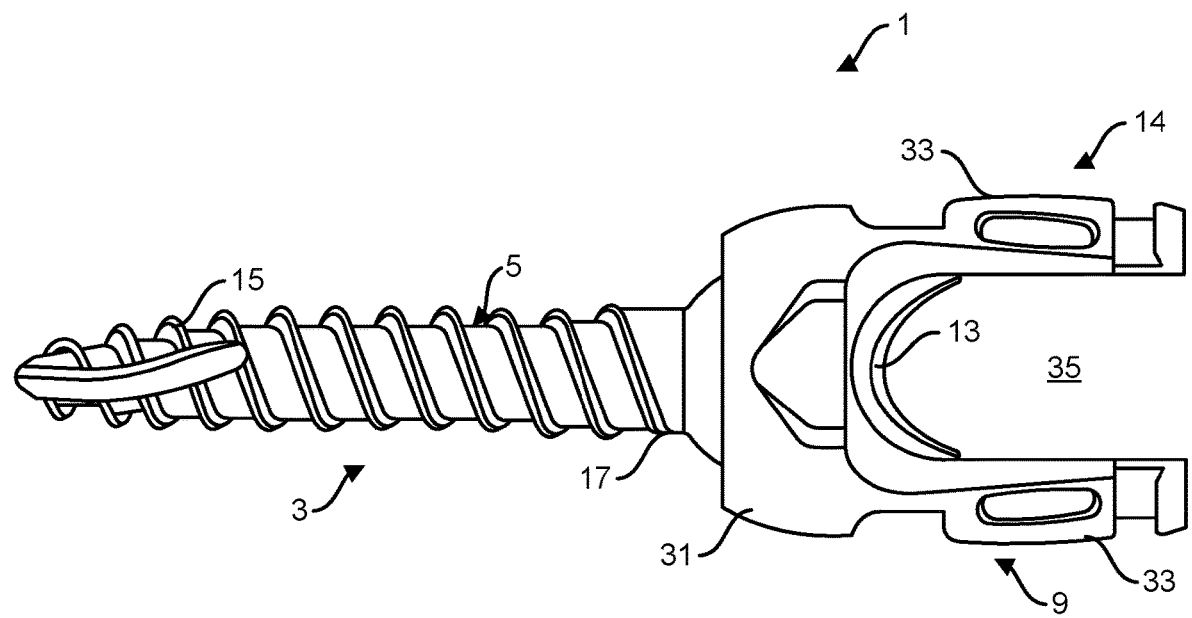
FIG. 2 is a top view of the bone screw assembly.
Figure 3:
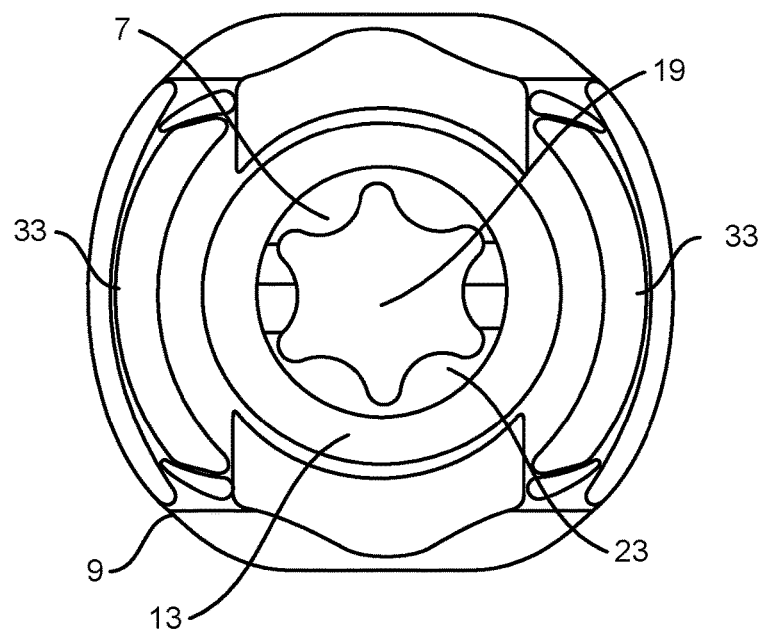
FIG. 3 is an end view of the bone screw assembly.

Referring to FIGS. 1-6 of the drawings, a first embodiment of a bone screw assembly is generally indicated at reference numeral 1. The assembly 1 includes a fastener 3 for anchoring the assembly 1 to a subject's bone (e.g., vertebra). In the illustrated embodiment, the fastener 3 includes a shaft 5 and a head 7 disposed on the shaft. The fastener 3 is received within a receiver 9 to mount the receiver onto the fastener such that the receiver can be rotated and pivoted around the head 7 of the fastener. A retaining ring 11 holds the fastener in the receiver 9. A saddle 13 is disposed in the receiver 9 above the retaining ring 11 and seats on top of the retaining ring. The receiver 9, retaining ring 11, and saddle 13 may be broadly considered a receiving assembly 14. The receiving assembly 14 may include fewer or additional components without departing from the scope of the disclosure. The receiving assembly 14 may be assembled prior to inserting the fastener 3 into the receiver 9. Further, the fastener 3 may be inserted into the vertebra prior to inserting the head 7 of the fastener into the receiver 9. Alternatively, the bone screw assembly 1 may be fully assembled prior to implantation of the fastener 3 in the vertebra.

The receiver 9 is configured to receive a rod (not shown) which sits on the saddle 13. A locking member (not shown) may be secured to the receiver 9 to retain the rod in the receiver. For example, a locking nut may be threaded in a top of the receiver 9 to engage the rod to fix the rod on the saddle 13 and in the receiver thereby fixing the rod relative to the vertebra. The fastener 3 and receiver 9 are movably coupled such that the fastener can be secured to the vertebrae in the orientation that is most suitable for the particular surgical procedure, and the retainer can be attached to the head 7 of the fastener 3 and rotated about the head to place the retainer in the desired position for receiving the rod before being fixed into place at the conclusion of the surgical procedure.

Figure 4:
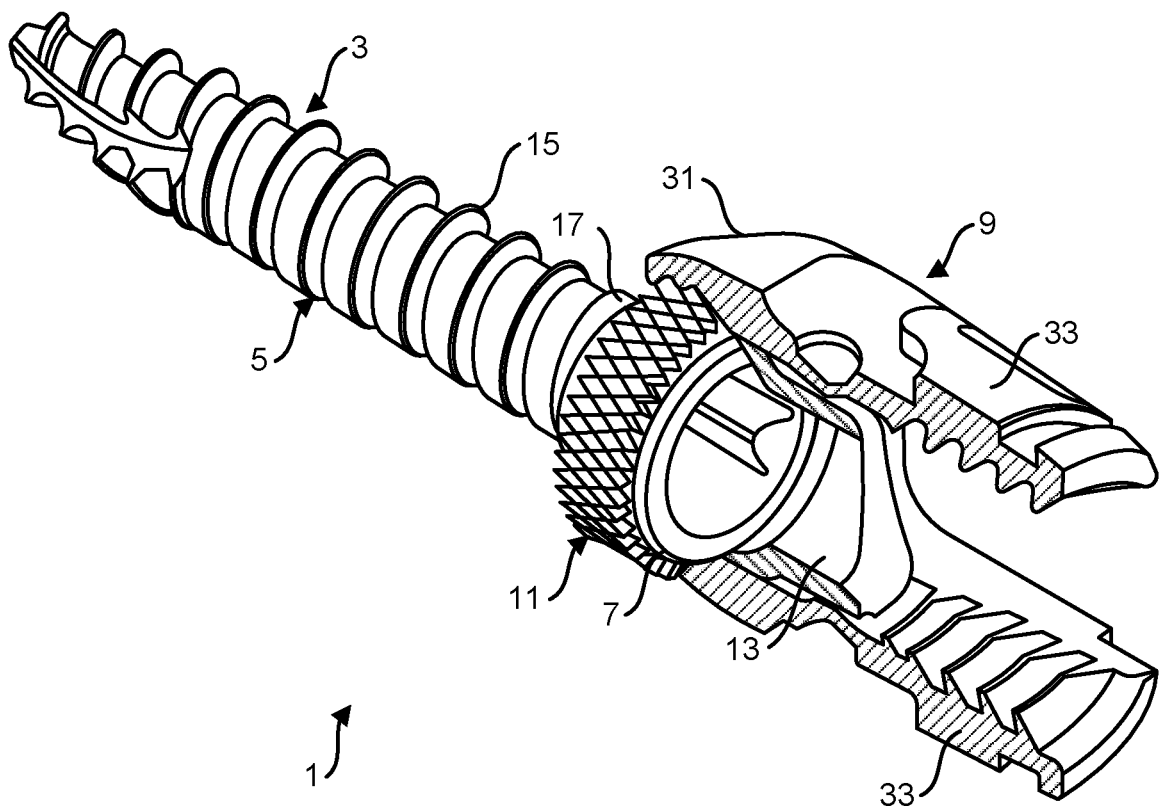
FIG. 4 is a perspective of the bone screw assembly with portions removed to show hidden detail.
Figure 5:
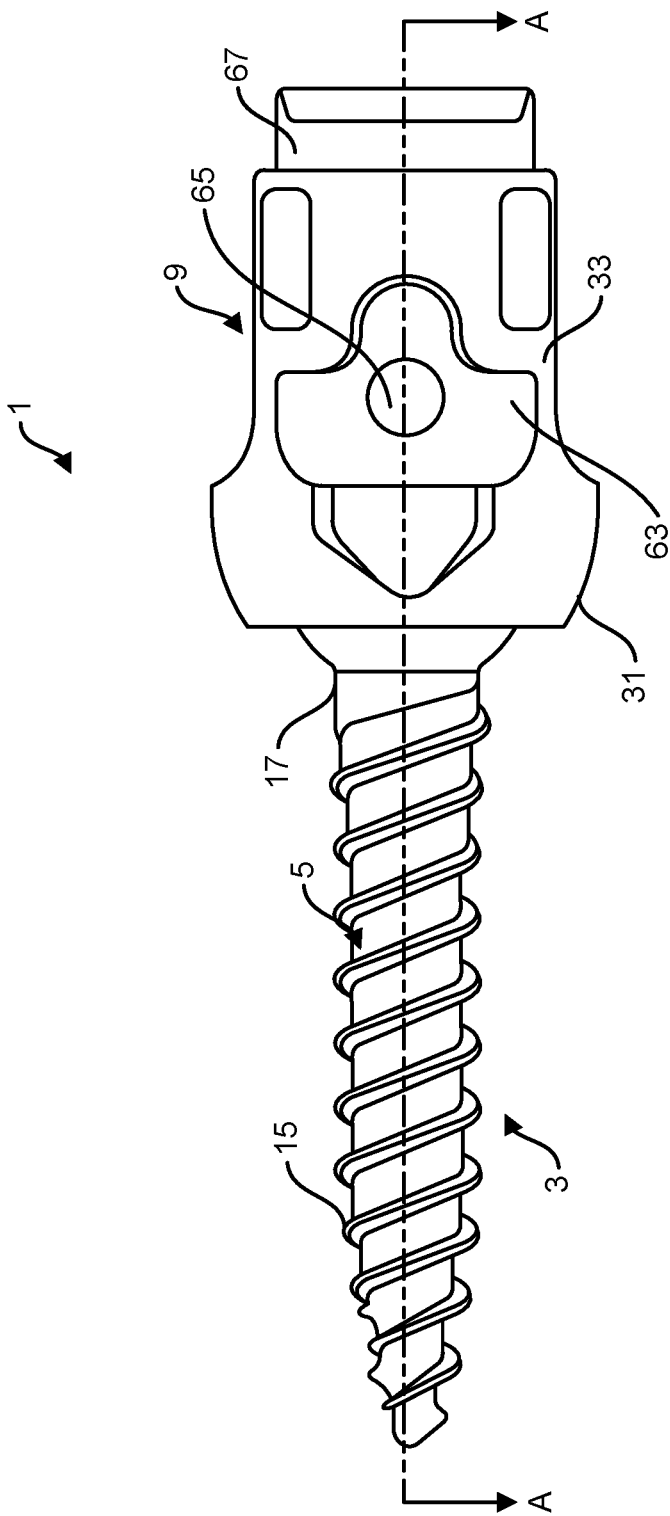
FIG. 5 is a side view of the bone screw assembly.
Figure 6:
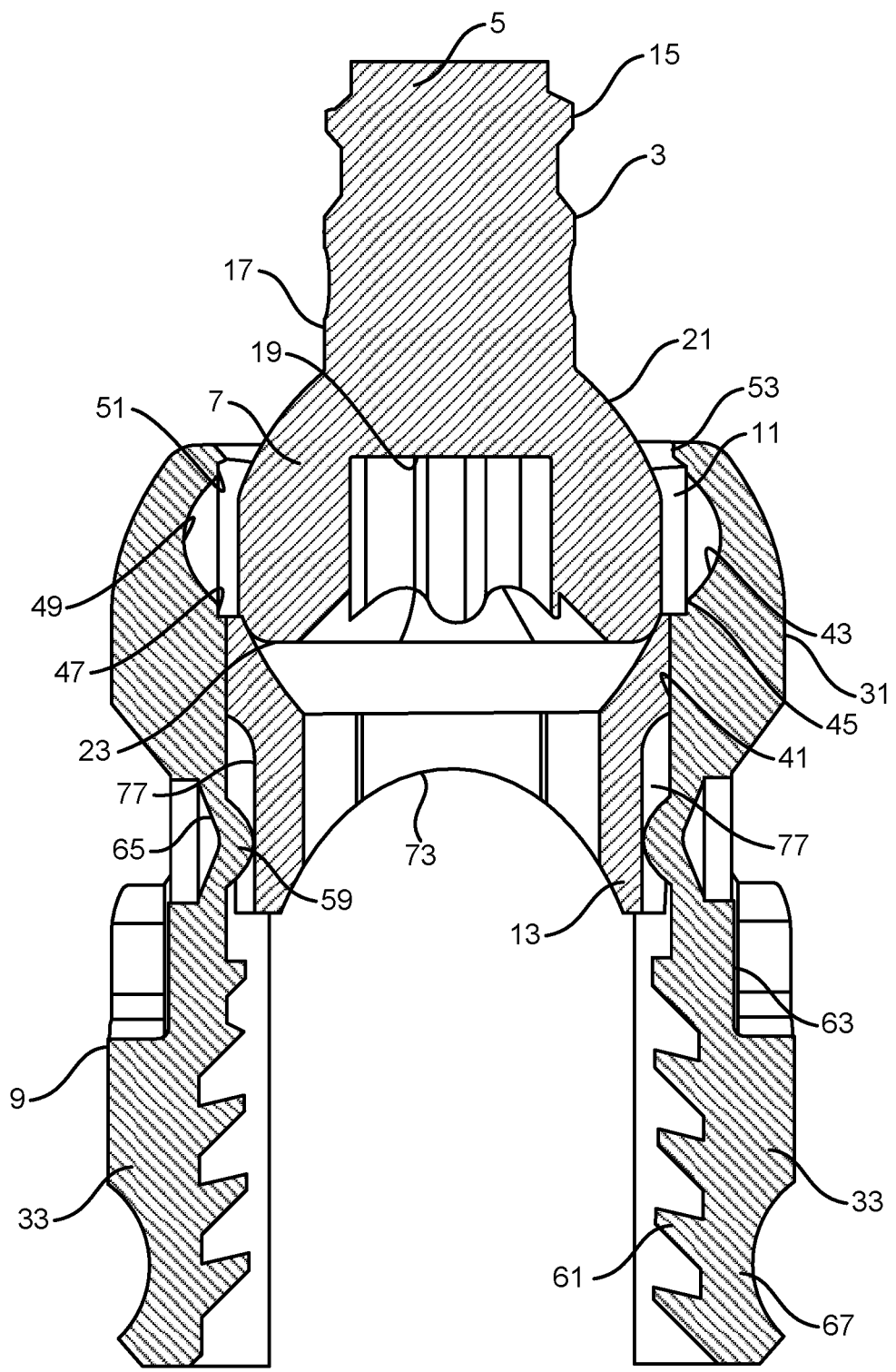
FIG. 6 is a section of a fragmentary portion of the bone screw assembly taken through line A-A in FIG. 5.
Figure 7:
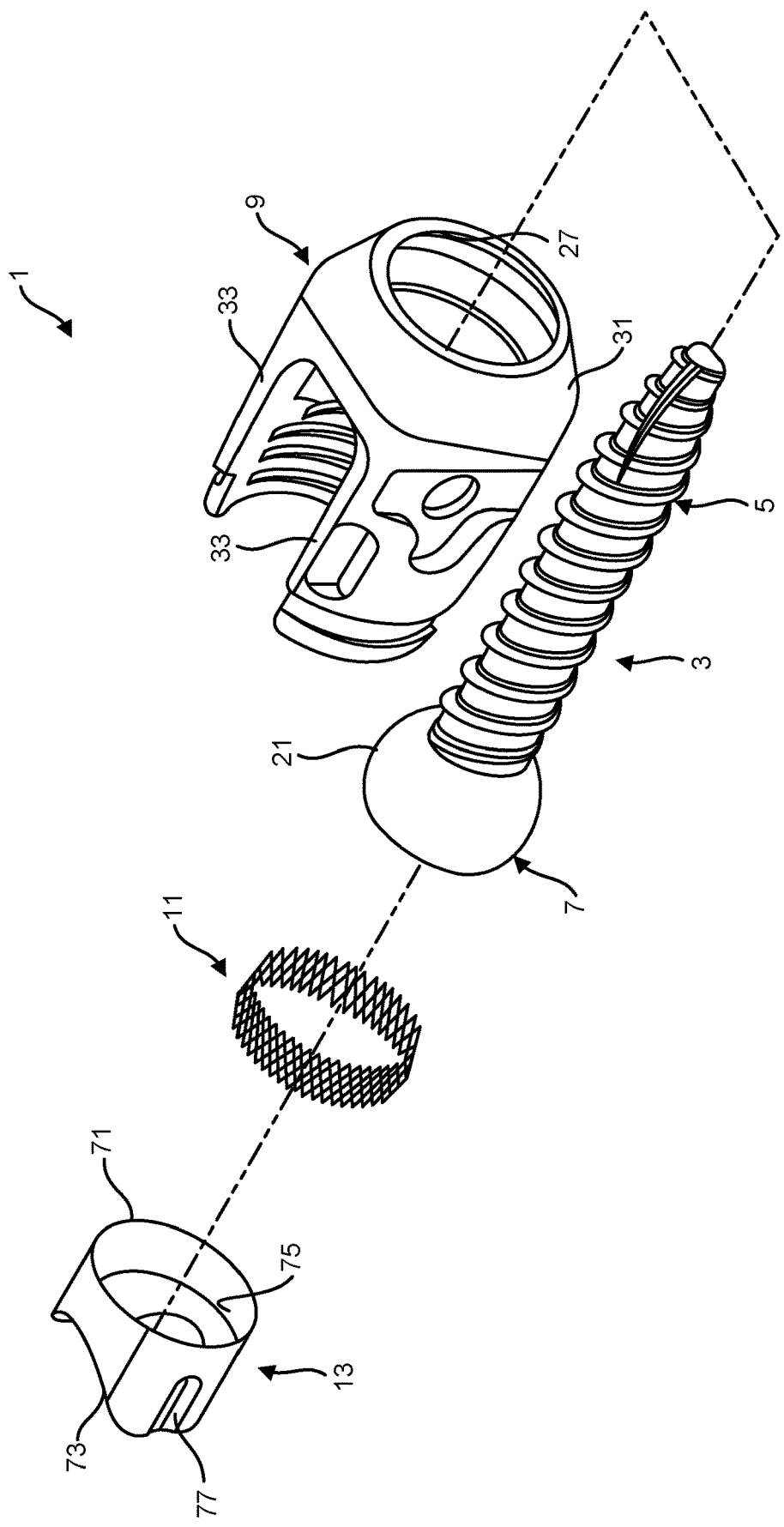
FIG. 7 is an exploded view of the bone screw assembly.

Referring to FIGS. 4, 6, and 7, the fastener 3 comprises an elongate structure defined in part by the shaft 5. A helical thread 15 is formed on the shaft 5 and extends generally from a shank portion 17 of the shaft to a tip of the shaft. The shank portion 17 extends axially upward from the threaded portion 15 of the shaft 5 to the head 7. In the illustrated embodiment, the head 7 has a semi-spherical shape with a receptacle 19 formed in a top surface of the head. As is generally understood in the art, the threads 15 on the fastener 3 are used to advance the fastener into the vertebra leading with the tip of the shaft 5. The receptacle 19 in the head 7 of the fastener 3 is configured to receive a driver (not shown) for driving the fastener into the vertebrae. As explained above, the spherical shape of the head 7 of the fastener 3 configures the head for a rotatable and pivotable connection with the retainer 9. In particular, the head 7 has a circumferentially extending side surface 21 that forms part of a sphere and a top surface 23 that is generally flat. As will be explained in greater detail below, retaining ring 11 engages the circumferentially extending side surface 21 of the fastener head 7 to hold the fastener 3 in the receiver 9.

Referring to FIGS. 1, 2, and 4-7, the receiver 9 comprises a generally U-shaped body defining an open-ended top and an opening 27 formed at a bottom of the body. The fastener head 7 is inserted though the opening 27 at the bottom of the body and held in the receiver 9 by the retaining ring 11, as will be explained in greater detail below. Open-ended screw assemblies of this type facilitate connection of rods to the screw assembly by allowing the rod to be oriented generally perpendicular to an axis of the receiver 9 and placed through the open top of the receiver rather than having to be inserted through a side hole in a closed-top receiver. The receiver 9 comprises a base 31 and a pair of opposing arms 33 projecting upwardly from the base and forming a channel 35 extending across the receiver between the arms. The base 31 is generally cylindrical and has a circumferentially extending inner surface and a circumferentially extending outer surface. A cross-sectional dimension of the base 31 widens at the outer surface from a bottom of the base to a top of the base. The inner surface of the base 31 comprises an upper portion 41 having a constant inner diameter, and a lower portion 43 having an inner diameter that varies along its length. In particular, a first section 45 of the lower portion 43 extends downward from the upper portion 41 and has a constant diameter. The first section 45 of the lower portion 43 is recessed from the upper portion 41 forming a ridge 47 between the upper portion 41 and lower portions 43. A second section 49 extends from the first section 45 and is defined by a rounded annular recess. A third section 51 extends from the second section 49 and comprises a constant diameter section. A fourth section 53 extends from the third section 51 and is defined by an annular projecting surface. The inner surface 37 of the base 31 is sized to receive the retaining ring 11 and the head 7 of the fastener 3 generally at the lower portion 43 of the base 31. The base of the receiver 9 also receives a bottom portion of the saddle 13 at the upper portion 41 of the base 31. Alternatively, the inner surface 37 of the base 31 may taper inward from a top of the base to a bottom of the base.

Each arm 33 has an inner surface and an outer surface. A detent 59 is disposed on a bottom section of the inner surface of each arm 33 and is configured to engage an upper portion of the saddle 13, as will be explained in greater detail below. An upper section of the inner surface of each arm 33 includes threads 61 configured to engage the locking member for securing a rod in the receiver 9. The outer surface of each arm 33 includes an indentation 63 that may provide a surface to grip the receiver 9 when attaching the receiver to the fastener 3. A tool receiving aperture 65 is formed in the indentation 63. In the illustrated embodiment, the tool receiving aperture 65 is a circular recess. However, the aperture 65 could have any shape for mating with a desired tool. An annular recess 67 may also be formed in the outer surface of the receiver 9 near a top of the receiver.

Referring to FIGS. 4, 6, and 7, the retaining ring 11 comprises an annular wire lattice member. The wire lattice construction configures the retaining ring 11 to be diametrically and circumferentially expandable to receive the head 7 of the fastener 3. As shown in the illustrated embodiment, the retaining ring 11 is held between the ridge 47 and annular projecting surface 53 of the base 31 of the retainer 9 generally preventing the retaining ring from sliding up and down relative to the retainer. In the illustrated embodiment, the retaining ring 11 has a diamond shaped wire lattice construction. However, other lattice shapes and retaining ring configurations are envisioned within the scope of the disclosure. For example, the retaining ring 11 may have a funnel or frustoconical shape such that a cross sectional dimension of the ring is smaller at a bottom of the ring than at a top of the ring. Further, the retaining ring 11 may be formed from any suitable material. In one embodiment, the retaining ring 11 is formed from Nitinol.

Referring to FIGS. 1, 2, 4, 6, and 7, the saddle 13 comprise a hollow cylindrical member formed separately from the retainer 9 and received in the retainer. A bottom edge 71 of the saddle 13 has a generally circular cross sectional shape configuring the saddle to have a level bottom surface for sitting the saddle on the retaining ring 11. A top edge 73 of the saddle 13 includes a pair of opposing U-shaped recessed sides forming a U-shaped receiving surface (broadly, a cradle) for receiving a rod member. An interior surface 75 of the saddle 13 tapers from the bottom edge 71 toward the top edge 73. In particular, the interior surface 75 curves inward from the bottom edge 71 to an intermediate position between the bottom edge and the top edge 73. The section of the interior surface 75 between the intermediate position and the top edge 73 has a generally constant internal diameter. A pair of opposing longitudinally extending indentations 77 are formed in an outer surface of the saddle 13 and extend from the top edge 73 toward the bottom edge 71. The indentations 77 are configured to receive a respective detent 59 on the retainer 9 for guiding movement of the saddle 13 relative to the retainer, as will be explained in greater detail below.

To assemble the bone screw assembly 1, the saddle 13 is inserted into the retainer 9 and positioned such that the longitudinally extending indentations 77 in the saddle 13 are aligned with the detents 59 on the receiver. Prior to or after inserting the saddle 13, the retaining ring 11 is inserted into the retainer 9 and placed between the ridge 47 and the annular projecting surface 53 on the base 31. With the retaining ring 11 secured in the base 31 of the receiver 9, the saddle 13 is captured within the receiver. In particular, the retaining ring 11 prevents the saddle 13 from falling out of the opening 27 in the bottom of the receiver 9, and the detents 59 on the receiver are engageable with a bottom end of the indentations 77 in the saddle to prevent the saddle from being pulled through the open top end of the receiver. However, the construction permits the saddle 13 to slide up and down within the receiver 9. The head 7 of the fastener 3 can then be inserted into the opening 27 in the bottom of the receiver 9 and engaged with an inner surface of the retaining ring 11. Engagement of the fastener head 7 with the retaining ring 11 causes at least a portion of the retaining ring to expand outwardly into the rounded annular recess 49 allowing at least a portion of the fastener head to move past the retaining ring. Continued insertion of the fastener head 7 causes the head to engage the saddle 13 moving the saddle 13 upwards in the receiver 9. The movement of the saddle 13 is guided by the interaction between the detents 59 on the receiver 9 and the longitudinal indentations 77 in the saddle. Once the fastener head 7 is sufficiently inserted into the receiver 9, the retaining ring 11 contracts back to hold the fastener in the receiver while permitting the fastener to rotate and pivot within the base 31 of the receiver. A rod can then be inserted through the open top of the receiver 9 and into the channel 35 to rest on top of the saddle 13. A locking member can then be engaged with the arms 33 of the receiver 9 to engage the locking member with the rod and press the rod against the saddle 13.

Figure 8:
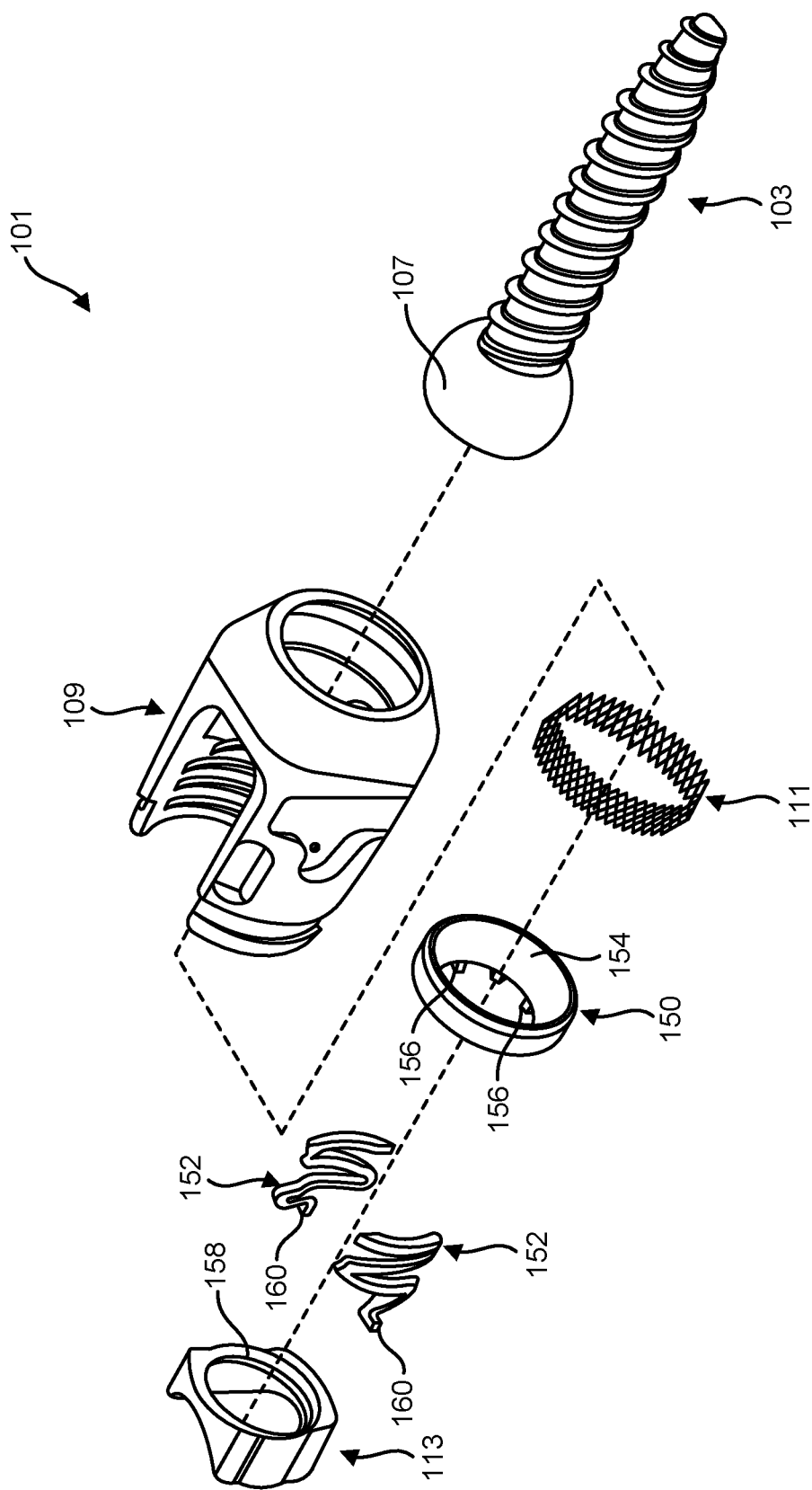
FIG. 8 is an exploded view of a bone screw assembly of another embodiment.
Figure 9:
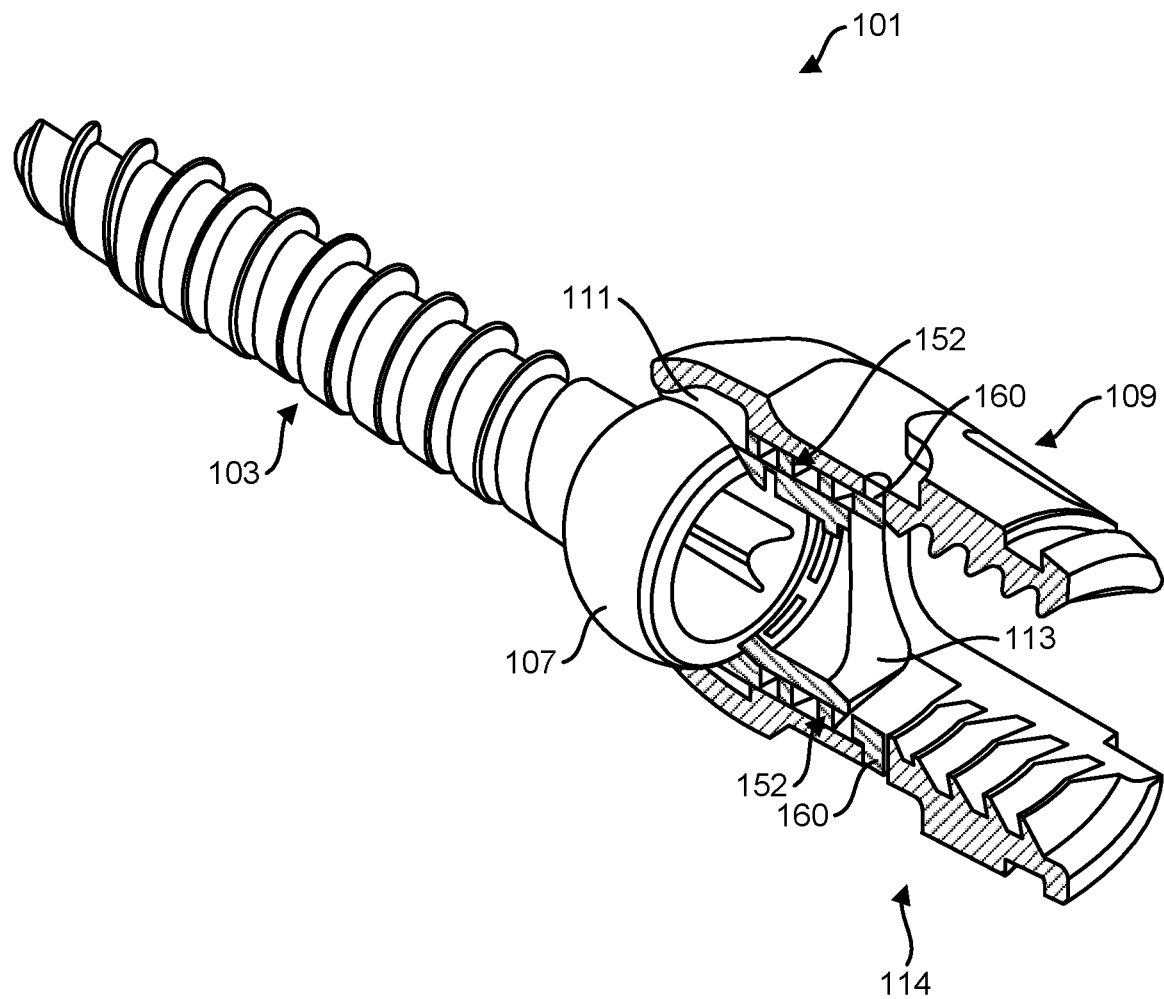
FIG. 9 is a perspective of the bone screw assembly of FIG. 8 with portions removed to show hidden detail.
Figure 10:
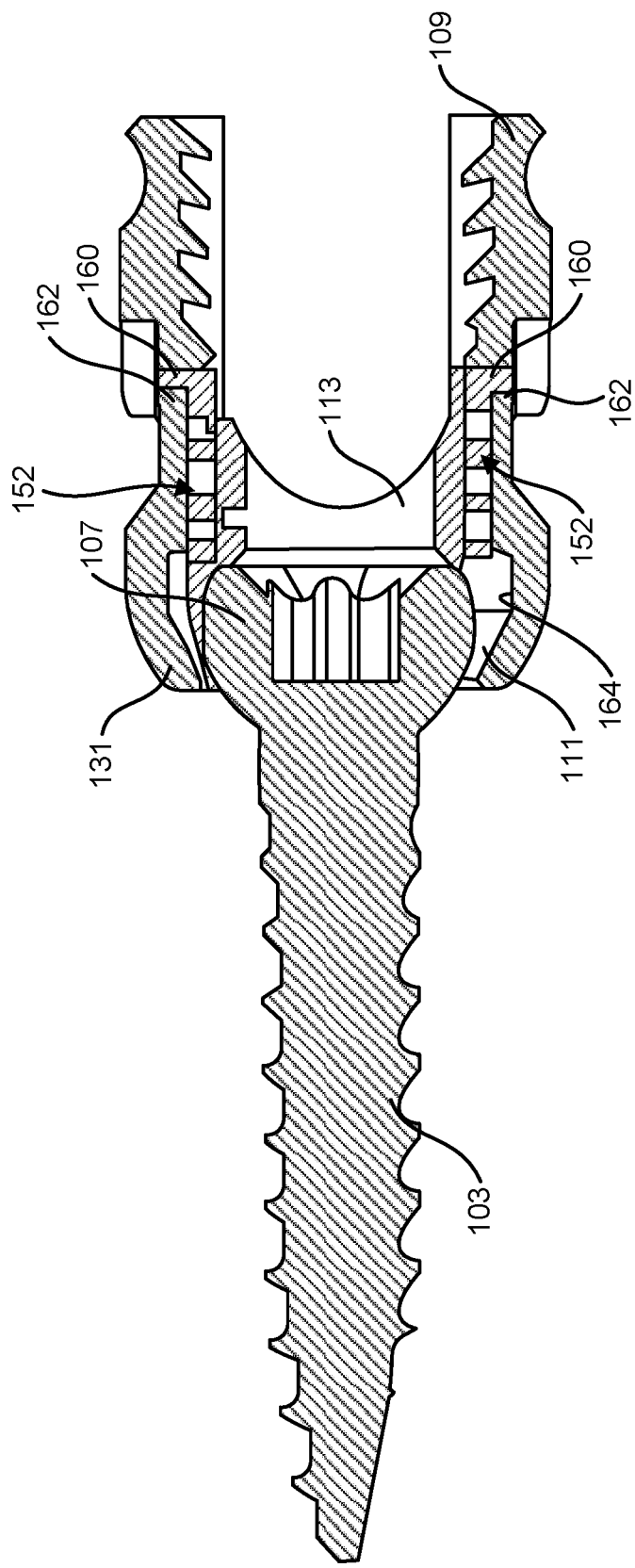
FIG. 10 is a section of the bone screw assembly of FIG. 8.

Referring to FIGS. 8-10, another embodiment of a bone screw assembly is generally indicated at reference numeral 101. The bone screw assembly 101 comprises a fastener 103 for anchoring the assembly 101 to a subject's bone (e.g., vertebra). The fastener 103 is received within a receiver 109 to mount the receiver on the fastener such that the receiver can be rotated and pivoted around a head 107 of the fastener. A retaining ring 111 holds the fastener in the receiver 109. A saddle 113 is disposed in the receiver 109. This bone screw assembly 101 is similar structurally to bone screw assembly 1. As such, the assembly 101 has essentially the same structural elements as assembly 1, which are indicated by corresponding reference numerals plus 100. Differences between bone screw assembly 101 and bone screw 1 are discussed below.

One difference between bone screw assembly 101 and bone screw assembly 1 is that the receiving assembly 114 further includes an insert 150 seated on top of the retaining ring 111, and a pair of springs 152 seated on top of the insert and extending along an outer surface of the saddle 113. Thus, the saddle 113 rests on the insert 150 rather than the retaining ring 111. The insert 150 is similar in construction to the bottom section of the saddle 13 of the first embodiment in that an inner surface 154 of the insert tapers inward from a bottom edge toward a top edge of the insert. In particular, the inner surface 154 curves inward from the bottom edge to the top edge. Hooks 156 extend from the top edge of the insert 150 and are circumferentially spaced around the insert 150. The hooks 156 are configured to be received in an annular recess 158 in an inner surface of the saddle 113 to couple the insert 150 to the saddle. The springs 152 comprise elongate spring members configured in a serpentine shape and having a projection 160 at a top of the spring member. The projection 160 is received in a hole 162 in the retainer 109 to attach the spring member to the retainer.

Insertion of the head 107 of the fastener 103 into the receiver 109 causes the head to engage an inner surface of the retaining ring 111 to expand an opening area of the retaining ring to allow the head to be inserted in to retaining ring. This engagement may also move the retaining ring 111 into an open space 164 in the base 131 of the receiver 109 to further provide clearance for the fastener head 107. Continued insertion of the head 107 causes the head to press against a bottom of the insert 150 thereby compressing the springs 152 to provide a sufficient clearance to fully insert the fastener head into the receiver 109. Once fully inserted, the retaining ring 111 is received around the head 107 of the fastener 103 and prevents the fastener from being pulled back out of the receiver 109. Further, the springs 152 exert a spring force on the insert 150 which in turn transfers the force to the head 107 of the fastener 103 to further secure the fastener to the receiver 109. The bone screw assembly 101 otherwise is configured and operates in substantially the same manner as bone screw assembly 1. The receiver 109, retaining ring 111, insert 150, springs 152, and saddle 113 may be broadly considered a receiving assembly 114. However, the receiving assembly 114 may include fewer or additional components without departing from the scope of the disclosure.

Figure 11:
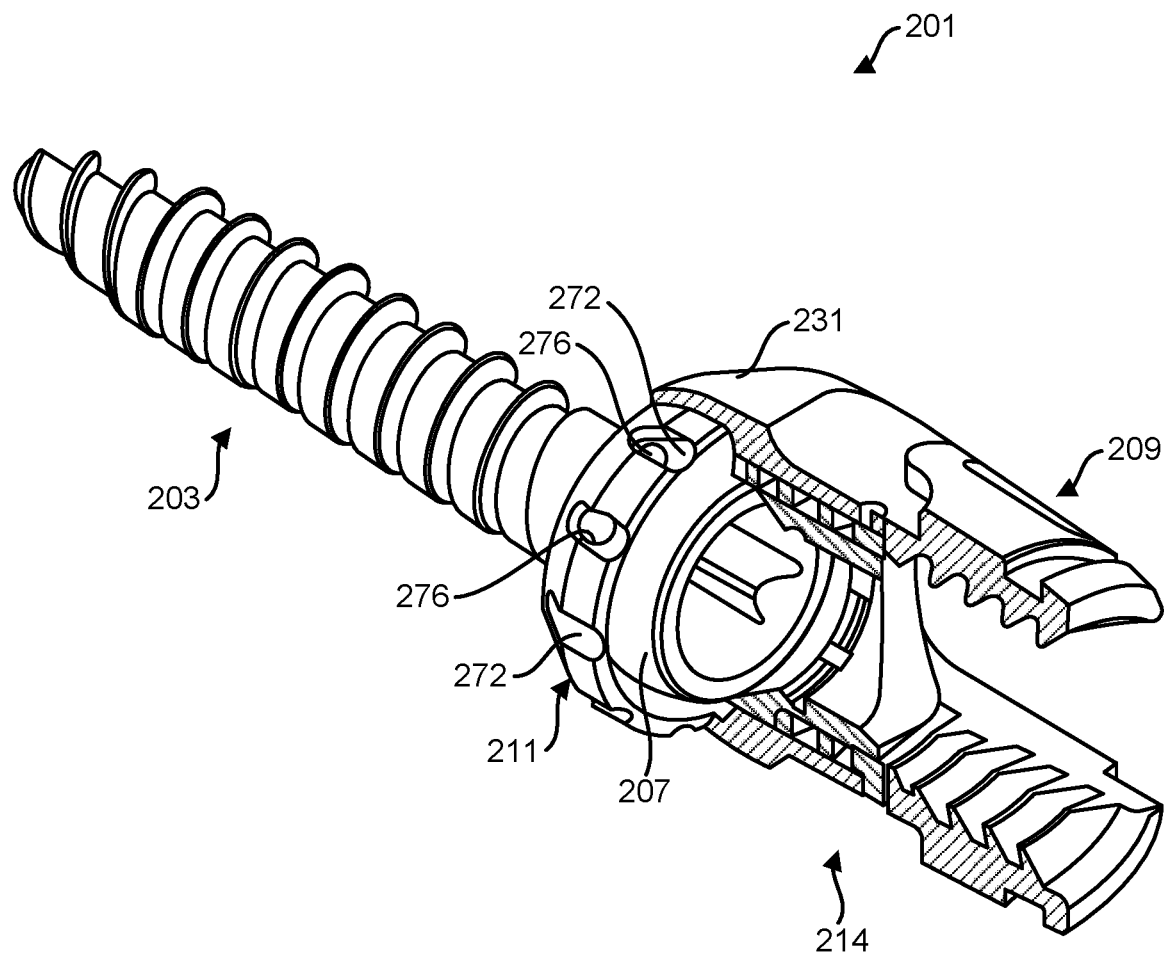
FIG. 11 is a perspective of a bone screw assembly of another embodiment with portions removed to show hidden detail.
Figure 12:
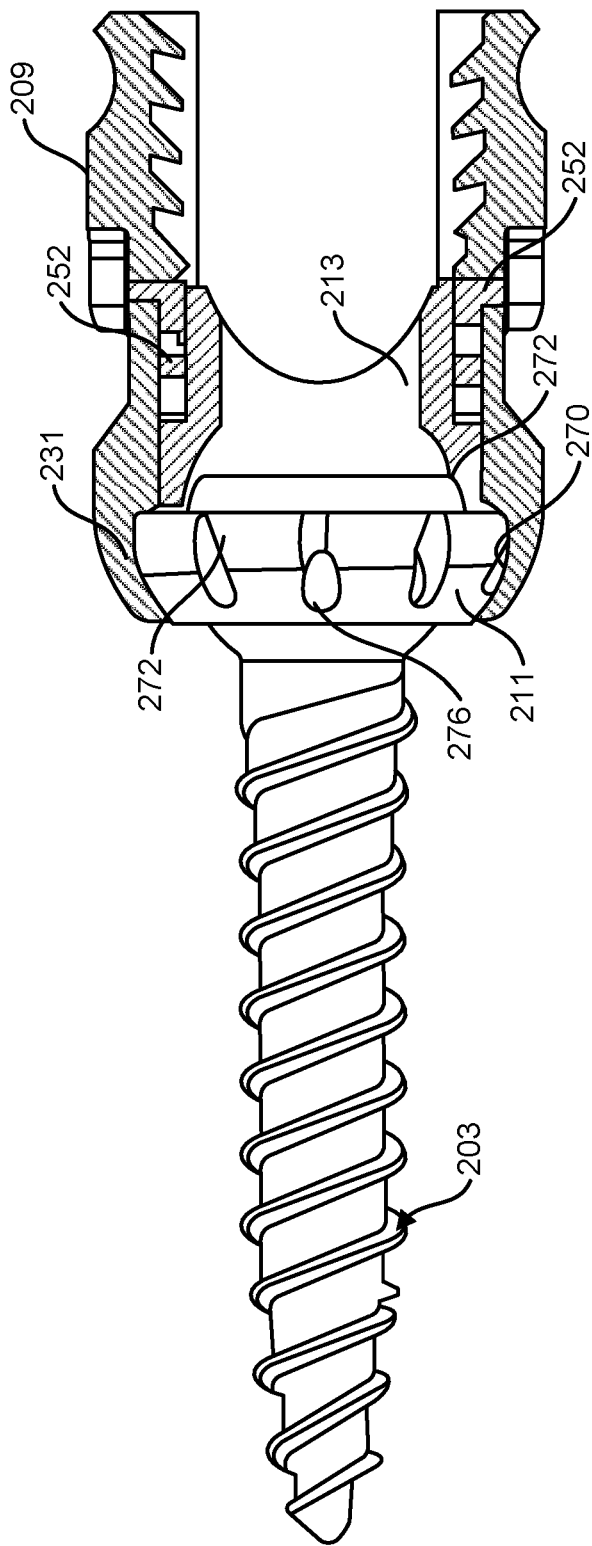
FIG. 12 is a side view of the bone screw assembly of FIG. 11.
Figure 13:
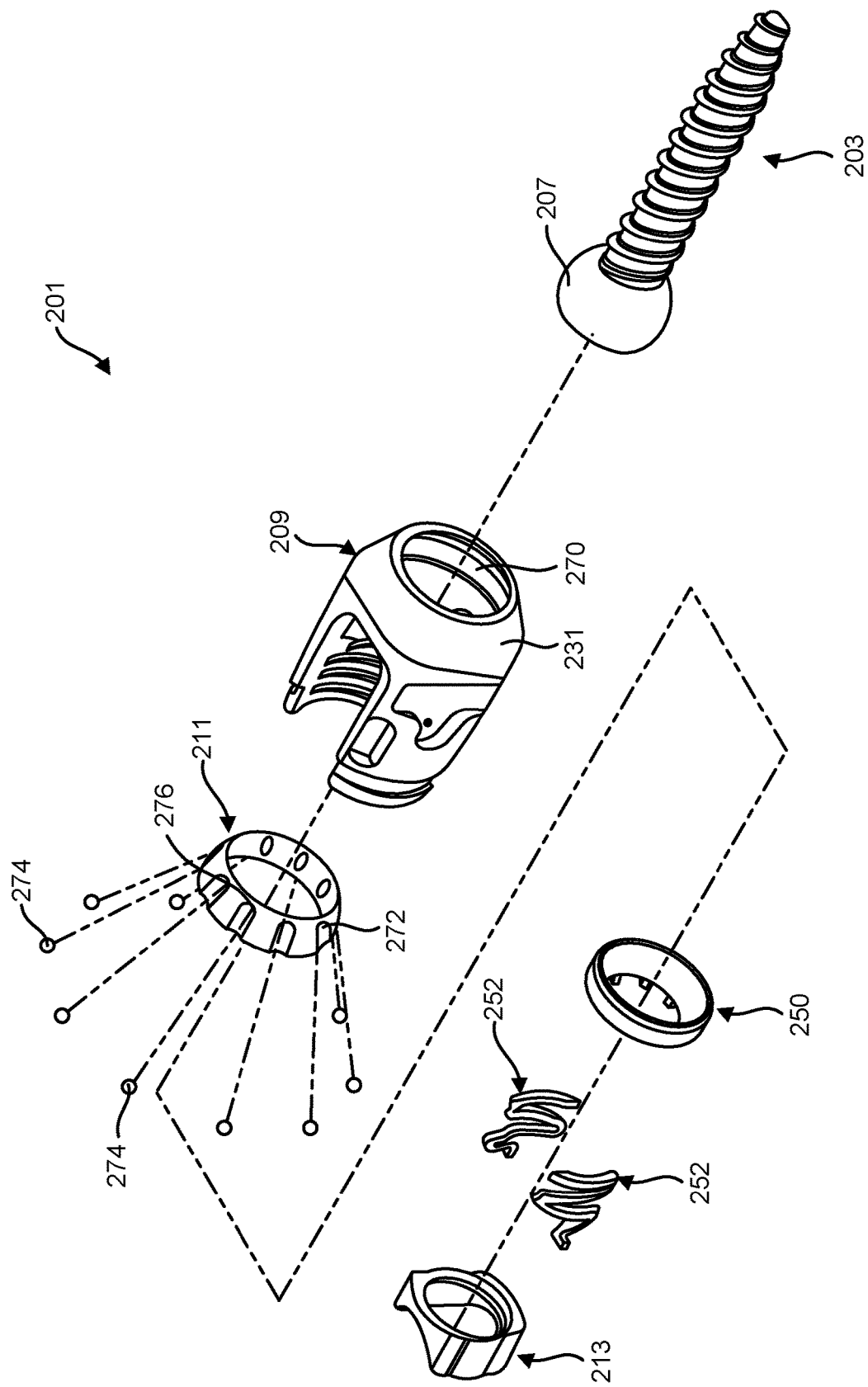
FIG. 13 is an exploded view of the bone screw of FIG. 11.

Referring to FIGS. 11-13, another embodiment of a bone screw assembly is generally indicated at reference numeral 201. The bone screw assembly 201 comprises a fastener 203 for anchoring the assembly 201 to a subject's bone (e.g., vertebra). The fastener 203 is received within a receiver 209 to mount the receiver on the fastener such that the receiver can be rotated and pivoted around a head 207 of the fastener. A retaining ring 211 holds the fastener in the receiver 209. An insert 250 is seated on top of the retaining ring 211. A saddle 213 is disposed in the receiver 209 and seats on top of the insert 250. A pair of springs 252 are also seated on top of the insert 250 and extend along an outer surface of the saddle 213. This bone screw assembly 201 is similar structurally to bone screw assembly 101. As such, the assembly 201 has essentially the same structural elements as assembly 101, which are indicated by corresponding reference numerals plus 100. Differences between bone screw assembly 201 and bone screw assembly 101 are discussed below.

The difference between bone screw assembly 201 and bone screw assembly 101 is that retaining ring 111 is replaced with retaining ring 211 which is fixedly received within a groove 270 in the base 231 of the receiver 209. The retaining ring 211 comprises a frustoconically shaped ring member having a plurality of circumferentially spaced channels 272 formed in an outer surface of the ring member. Balls 274 are received in the channels 272 and held in the channels by the surface of the groove 270 in the base 231. The channels 272 have openings 276 at a bottom of the channel that receive the balls 274. Thus, prior to insertion of the fastener head 207, the balls 274 rest at a bottom of the channels 272 creating an effective internal cross sectional dimension of the retaining ring 211 that is smaller than the cross sectional dimension of the top of the fastener head 207. However, the balls 274 are moveable within the channels 272 to provide a clearance for inserting the fastener head 207 into the receiver 209. In particular, insertion of the head 207 of the fastener 203 into the receiver 209 causes the head to press against an inner surface of the retaining ring 211 moving the balls 274 out of the openings 276 and into the channels 272. Because the surface of the groove 270 flares outward to match the frustoconical shape of the retaining ring 211, the balls 274 will ride up the channels 272 and out of the way of the fastener head 207 to allow at least a portion of the fastener head to be inserted past the balls. To this effect, the retaining ring 211 and balls 274 may be considered effectively expandable in that the opening area increases in response to engagement from the fastener head 207. After a sufficient portion of the fastener head 207 is inserted past the balls 274, the semi-spherical shape of the fastener head will provide clearance for the balls to move down the channels 272 and back into the openings 276. Therefore, once the fastener head 207 is sufficiently inserted into the receiver 209, the balls 274 will again reduce the effective cross sectional dimension of the retaining ring 211 preventing the fastener 3 from being pulled back out of the receiver 209. The bone screw assembly 201 otherwise is configured and operates in substantially the same manner as bone screw 101. The receiver 209, retaining ring 211, insert 250, springs 252, and saddle 213 may be broadly considered a receiving assembly 214. However, the receiving assembly 214 may include fewer or additional components without departing from the scope of the disclosure.

Figure 14:
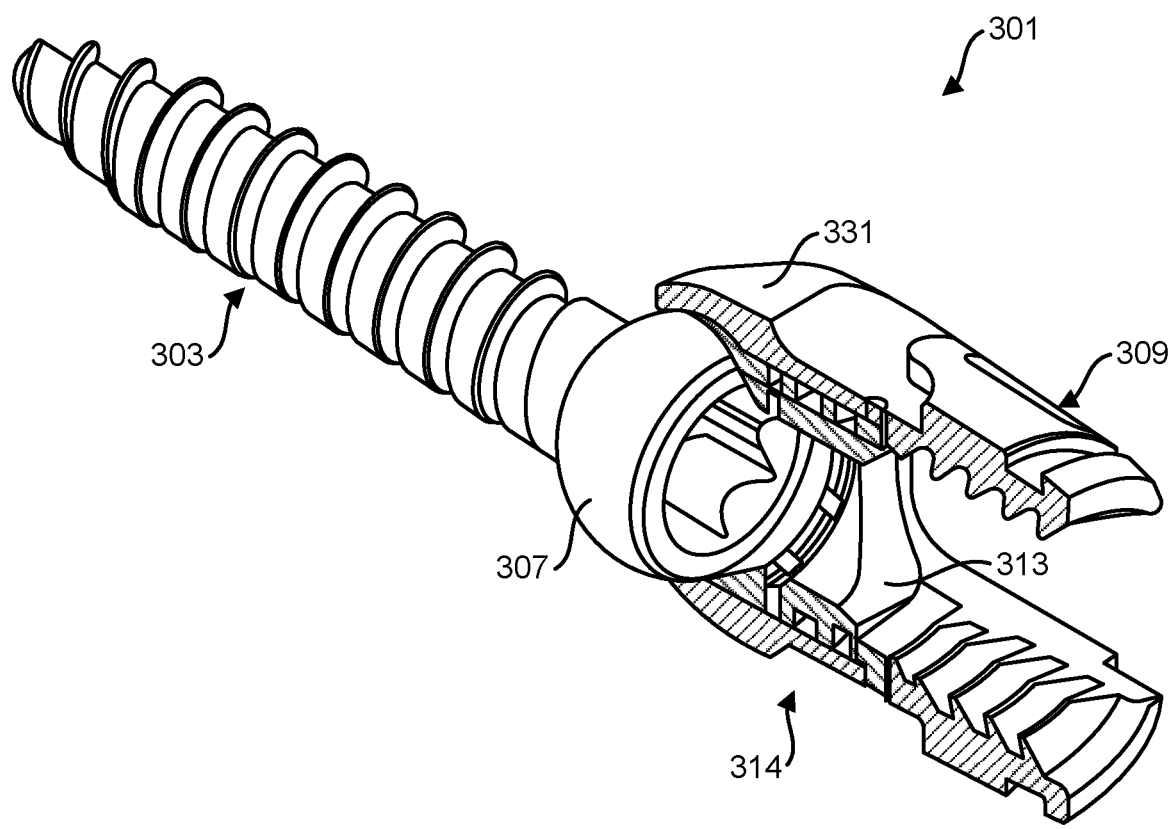
FIG. 14 is a perspective of a bone screw assembly of another embodiment with portions removed to show hidden detail.
Figure 15:
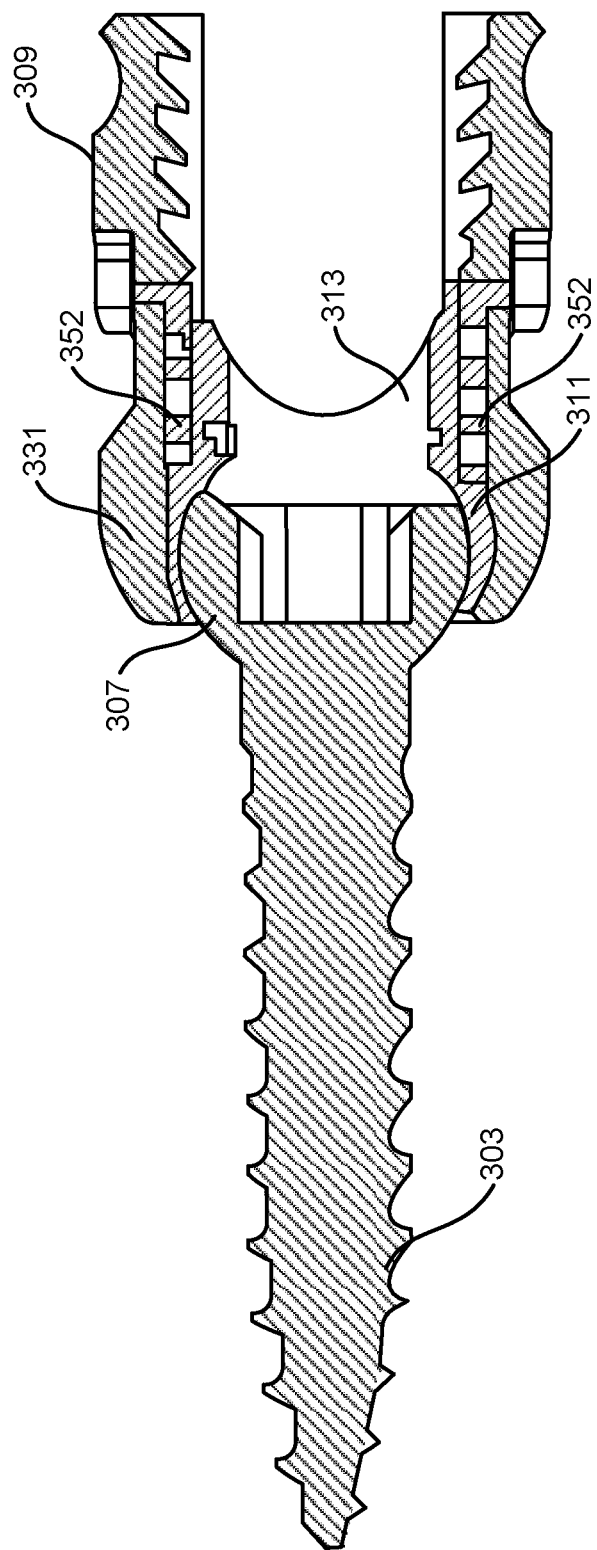
FIG. 15 is a section of the bone screw assembly of FIG. 14.
Figure 16:
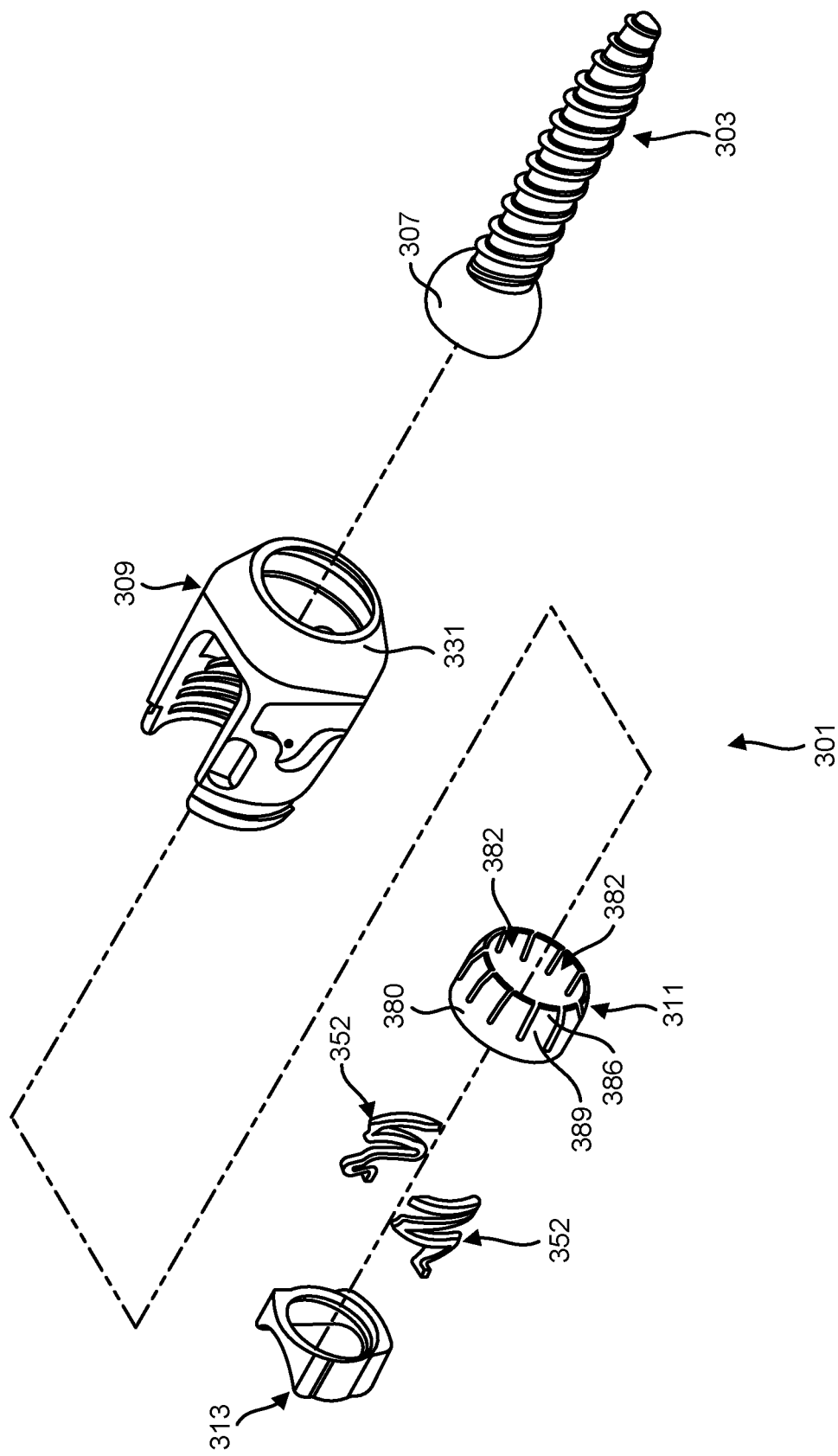
FIG. 16 is an exploded view of the bone screw assembly of FIG. 14.
Figure 17:
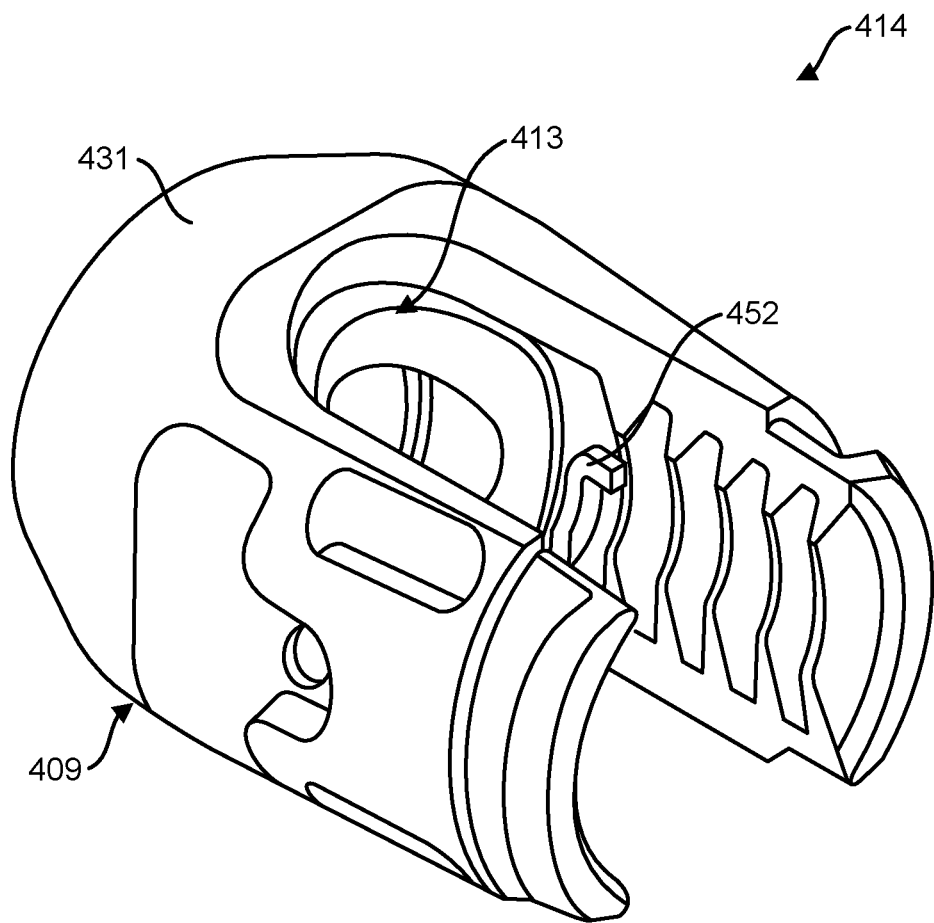
FIG. 17 is a perspective of a receiving assembly of another embodiment.
Figure 18:
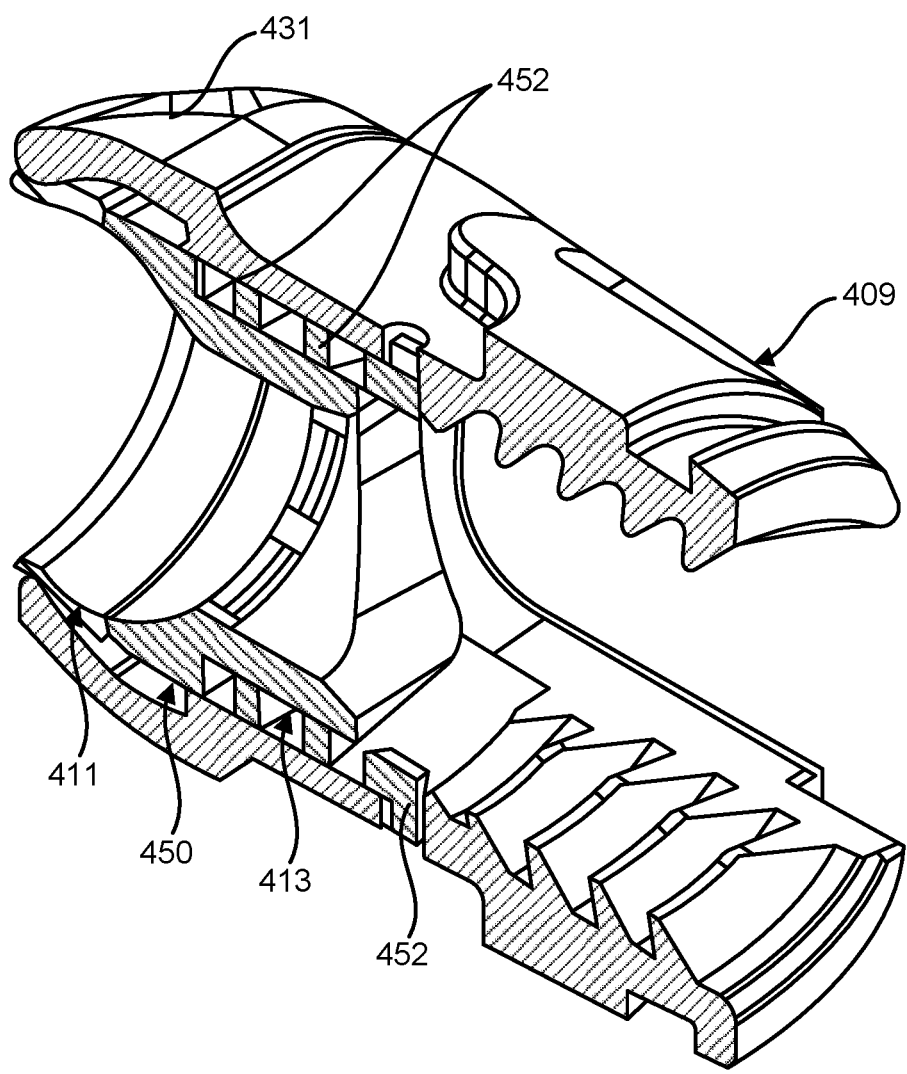
FIG. 18 is a fragmentary perspective of the receiving assembly of FIG. 17.
Figure 19:
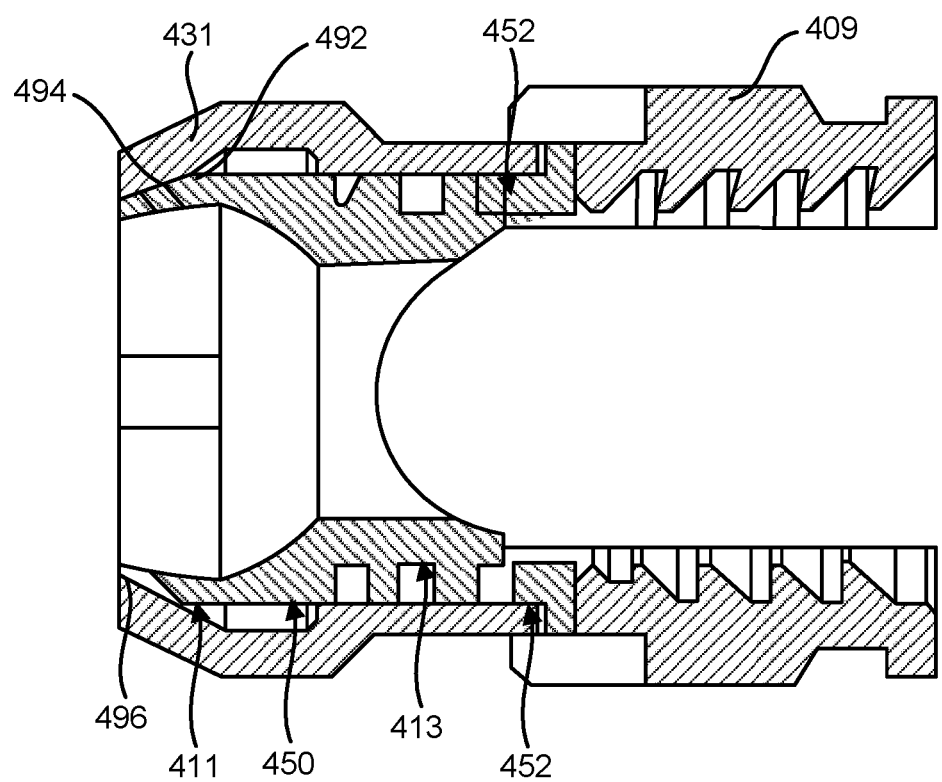
FIG. 19 is a section of the receiving assembly of FIG. 17.
Figure 20:
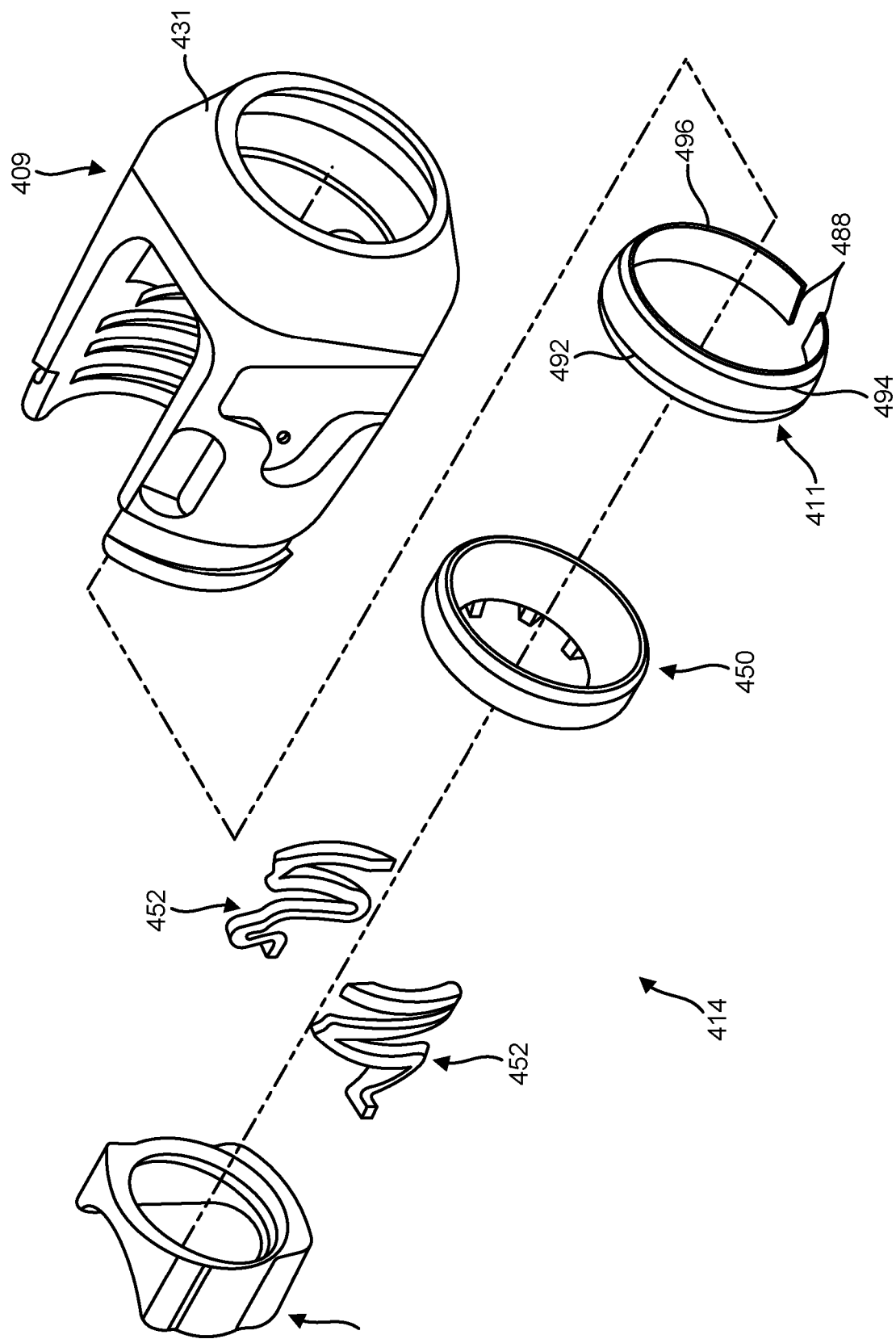
FIG. 20 is an exploded view of the receiving assembly of FIG. 17.

Referring to FIGS. 14-16, another embodiment of a bone screw assembly is generally indicated at reference numeral 301. The bone screw assembly 301 comprises a fastener 303 for anchoring the assembly 301 to a subject's bone (e.g., vertebra). The fastener 303 is received within a receiver 309 to mount the receiver on the fastener such that the receiver can be rotated and pivoted around a head 307 of the fastener. A retaining ring 311 holds the fastener in the receiver 309. A saddle 313 is disposed in the receiver 309 and seats on top of the retaining ring 311. A pair of springs 352 are also seated on top of the retaining ring 311 and extend along an outer surface of the saddle 313. This bone screw assembly 301 is similar structurally to bone screw assembly 201. As such, the assembly 301 has essentially the same structural elements as assembly 201, which are indicated by corresponding reference numerals plus 100. Differences between bone screw assembly 301 and bone screw assembly 201 are discussed below.

One difference between bone screw assembly 301 and bone screw assembly 201 is that insert 250 is removed and retaining ring 211 is replaced with retaining ring 311. The retaining ring 311 comprises a ring member including a continuous annular portion 380 and a plurality of circumferentially spaced fingers 382 extending away from the annular portion. Each finger 382 includes a first portion 384 that extends from the annular portion 380 generally parallel to a central axis of the retaining ring 311, and a second portion 386 that extends at an angle from the first portion toward the central axis of the retaining ring. Insertion of the head 307 of the fastener 303 into the receiver 309 causes the head to press against the fingers 382 on the retaining ring 311 causing the fingers to flex outwardly to provide a clearance for the head to pass the fingers. To this effect, the retaining ring 311 may be considered effectively expandable in that the opening area increases in response to engagement from the fastener head 307. Once the fastener head 307 is sufficiently inserted into the retaining ring 311, the fingers 382 will flex back into their pre-engaged configuration preventing the fastener head 307 from being withdrawn from the receiver 309. In particular, the fingers 382 are captured between the head 307 and the base 331 of the receiver 309 thereby reducing the effective opening size of the receiver. For example, at least a portion of the head 307 of the fastener 303 is wider than the effective opening of the receiver 309 preventing the head from passing out of the opening. The bone screw assembly 301 otherwise is configured and operates in substantially the same manner as bone screw 201. The receiver 309, retaining ring 311, springs 352, and saddle 313 may be broadly considered a receiving assembly 314. However, the receiving assembly 314 may include fewer or additional components without departing from the scope of the disclosure.

Referring to FIGS. 17-20, another embodiment of a receiving assembly is generally indicated at reference numeral 414. A receiver 409 is configured to receive a head of a fastener (not shown) to mount the receiver on the fastener such that the receiver can be rotated and pivoted around the head of the fastener. A retaining ring 411 holds the fastener in the receiver 409. An insert 450 is seated on top of the retaining ring 411. A saddle 413 is disposed in the receiver 409 and seats on top of the insert 450. A pair of springs 452 are also seated on top of the insert 450 and extend along an outer surface of the saddle 413. This receiving assembly 414 is similar structurally to receiving assembly 214. As such, the assembly 414 has essentially the same structural elements as assembly 214, which are indicated by corresponding reference numerals plus 200. Differences between receiving assembly 414 and receiving assembly 214 are discussed below.

The difference between receiving assembly 414 and receiving assembly 214 is that retaining ring 211 is replaced with retaining ring 411. The retaining ring 411 comprises a discontinuous ring member having a pair of free ends 488. The retaining ring 411 has a generally frustoconical shape whereby a cross sectional dimension of the retaining ring at a top of the ring is greater than a cross sectional dimension of the retaining ring at a bottom of the ring. Further, an outer surface of the retaining ring 411 includes a first section 492 that extends axially from a top of the ring, a second portion 494 that extends inward at an angle from the first portion, and a third portion 496 that extend axially from the second portion. Inserting the fastener head into the receiver 409 will engage the fastener head with the retaining ring 411 causing the retaining ring to expand through the movement of the free ends 488 away from each other allowing at least a portion of the fastener head to move past the retaining ring. Continued insertion of the fastener head causes the head to engage the insert 450 moving the insert upwards in the receiver 409 against the bias of the springs 452. Once the fastener head 407 is sufficiently inserted into the receiver 409, the retaining ring 411 contracts back to its pre-engaged configuration to hold the fastener in the receiver while permitting the fastener to rotate and pivot within the base 431 of the receiver. Further, the outer surface of the retaining ring 411, and in particular the second portion 494, engages the inner surface of the base 431 of the receiver 409 to prevent the fastener from being pulled out of the receiver 409. The springs 452 also exert a spring force on the insert 450 which in turn transfers the force to the head of the fastener to further secure the fastener to the receiver 409. The receiving assembly 414 otherwise is configured and operates in substantially the same manner as receiving assembly 214. Additionally, the receiving assembly 414 may include fewer or additional components without departing from the scope of the disclosure.

Figure 21:
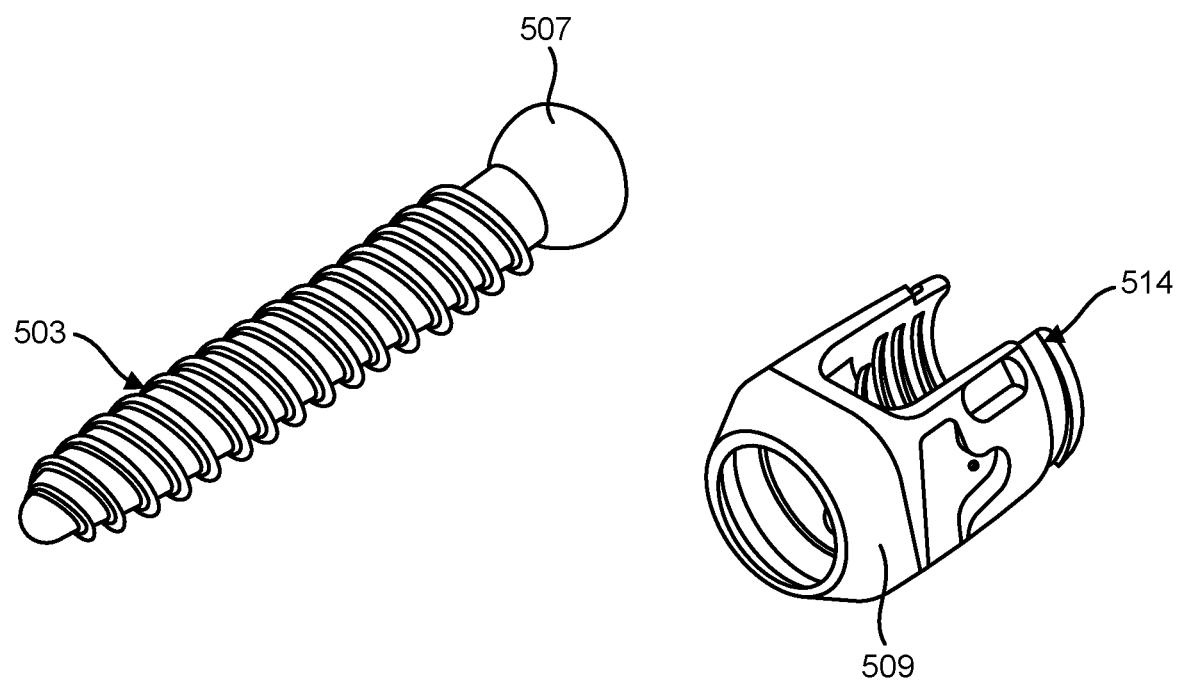
FIG. 21 is an exploded view of a bone screw assembly of another embodiment.
Figure 22:
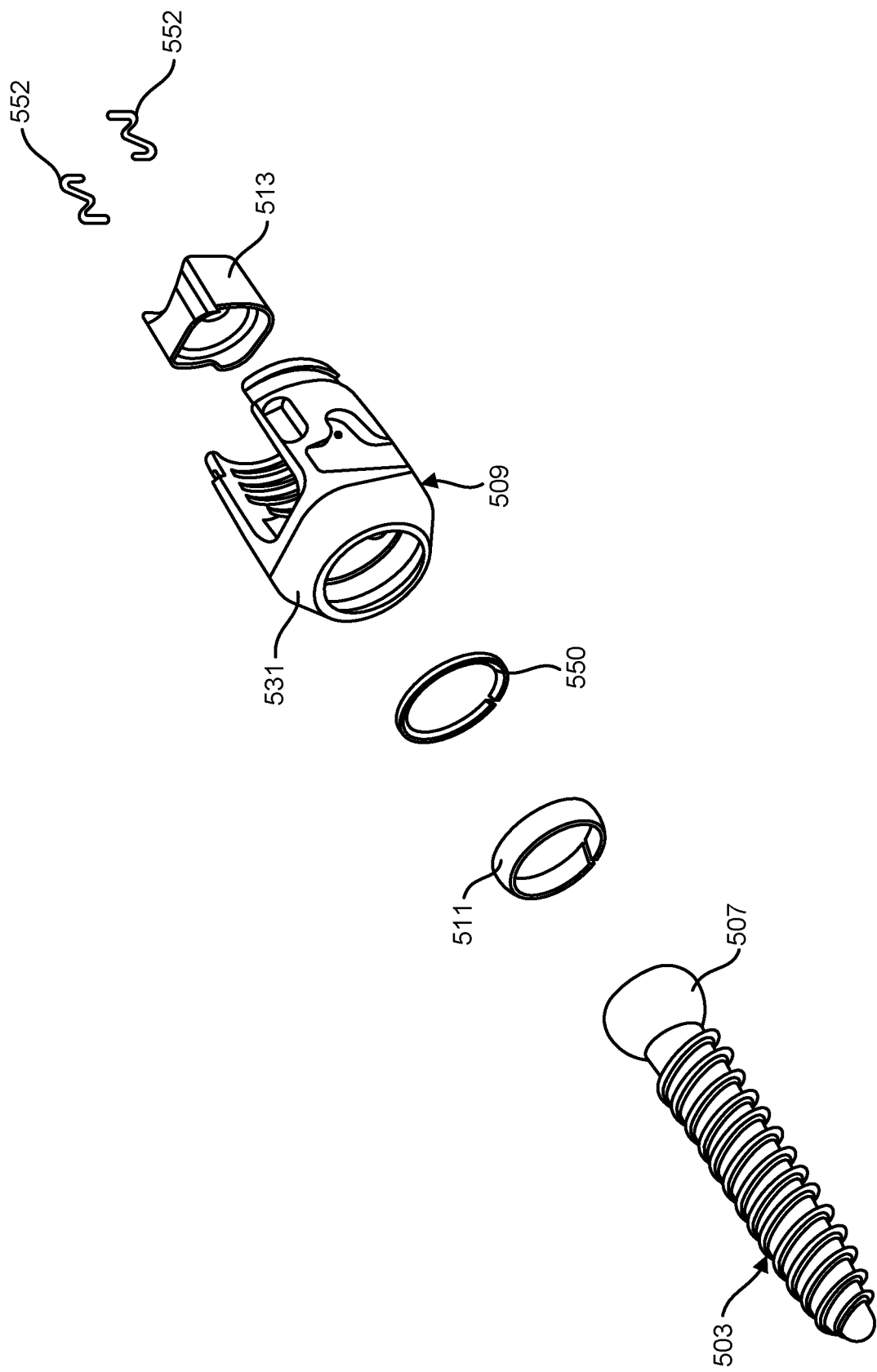
FIG. 22 is another exploded view of a bone screw assembly of FIG. 21.

Referring to FIGS. 21 and 22, another embodiment of a bone screw assembly is generally indicated at reference numeral 501. The bone screw assembly 501 comprises a fastener 503 for anchoring the assembly 501 to a subject's bone (e.g., vertebra). The fastener 503 is received within a receiver 509 to mount the receiver on the fastener such that the receiver can be rotated and pivoted around a head 507 of the fastener. A retaining ring 511 holds the fastener in the receiver 509. An insert 550 is seated on top of the retaining ring 511. A saddle 513 is disposed in the receiver 509 and seats on top of the insert 550. A pair of springs 552 are also seated on top of the insert 550 and extend along an outer surface of the saddle 513. This receiving assembly 514 is similar structurally to receiving assembly 414. As such, the assembly 514 has essentially the same structural elements as assembly 414, which are indicated by corresponding reference numerals plus 100. Differences between receiving assembly 514 and receiving assembly 414 are discussed below.

The difference between receiving assembly 514 and receiving assembly 414 is that insert 450 is replaced with insert 550. The insert 550 comprises a discontinuous ring member having a pair of free ends. Inserting the fastener head into the receiver 509 will engage the fastener head with the retaining ring 511 causing the retaining ring to expand through the movement of the free ends away from each other allowing at least a portion of the fastener head to move past the retaining ring. Continued insertion of the fastener head causes the head to engage the insert 550 moving the insert upwards in the receiver 509 against the bias of the springs 552. Once the fastener head 507 is sufficiently inserted into the receiver 509, the retaining ring 511 contracts back to its pre-engaged configuration to hold the fastener in the receiver while permitting the fastener to rotate and pivot within the base 531 of the receiver. Further, the outer surface of the retaining ring 511 engages the inner surface of the base 531 of the receiver 509 to prevent the fastener from being pulled out of the receiver 509. The springs 552 also exert a spring force on the insert 550 which in turn transfers the force to the head of the fastener to further secure the fastener to the receiver 509. The receiving assembly 514 otherwise is configured and operates in substantially the same manner as receiving assembly 414. Additionally, the receiving assembly 514 may include fewer or additional components without departing from the scope of the disclosure.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A bone screw assembly comprising:
a fastener comprising a shaft and a head disposed on the shaft, the fastener being configured to be anchored within a subject's bone;
a receiving assembly configured to be movably mounted on the head of the fastener, the receiving assembly comprising a receiver disposable around at least a portion of the head of the fastener and defining a channel for receiving a rod member therein, a retaining ring disposed within the receiver for holding the head of the fastener in the receiver, an insert disposed in the receiver above the retaining ring, and a saddle disposed in the receiver above the insert, the saddle defining a cradle for seating the rod member in the receiver, the receiving assembly further comprising a pair of springs attached to the receiver above the insert, the springs comprising elongate spring members configured in a serpentine shape and biasing the insert toward the retaining ring.

2. The assembly set forth in claim 1, wherein the cradle includes a U-shaped receiving surface for seating the rod member.

3. The assembly set forth in claim 1, wherein the insert is coupled to the saddle such that the saddle and insert move together in the receiver.

4. The assembly set forth in claim 3, wherein the insert includes a plurality of hooks and the saddle defines an annular recess therein, the hooks being received in the annular recess to couple the insert to the saddle.

5. The assembly set forth in claim 1, wherein the retaining ring comprises Nitinol.

6. The assembly set forth in claim 1, wherein the retaining ring comprises a discontinuous ring member.

7. The assembly set forth in claim 1, wherein the retaining ring comprises a continuous ring member.

8. The assembly set forth in claim 1, wherein the insert comprises a discontinuous ring member.

9. A receiving assembly for a bone screw comprising:
a receiver configured to be movably mounted on a head of the bone screw, the receiver defining a channel for receiving a rod member therein;
a retaining ring disposed within the receiver for holding the head of the bone screw in the receiver;
an insert disposed in the receiver above the retaining ring; and
a saddle disposed in the receiver above the insert, the saddle defining a cradle for seating the rod member in the receiver;
wherein the retaining ring comprises a discontinuous ring member, and wherein the insert comprises a discontinuous ring member such that no portion of the insert extends continuously around an entire circumference of the insert.

10. The assembly set forth in claim 9, further comprising a pair of springs attached to the receiver above the insert, the springs biasing the insert toward the retaining ring.

11. A receiving assembly for a bone screw comprising:
a receiver configured to be movably mounted on a head of the bone screw, the receiver defining a channel for receiving a rod member therein; and
a continuous retaining ring disposed within the receiver for holding the head of the bone screw in the receiver, the continuous retaining ring being configured to expand a receiving area of the retaining ring to permit at least a portion of the head of the bone screw to be inserted through the retaining ring, wherein the retaining ring comprises a wire lattice.

12. The assembly set forth in claim 11, wherein the retaining ring comprises Nitinol.

13. The assembly set forth in claim 11, in combination with the bone screw.

14. The assembly set forth in claim 13, wherein the bone screw comprising the head and a shaft extending from the head, a helical thread being disposed on the shaft for advancing the bone screw into a subject's bone and a receptacle being formed in the head for receiving a driver for driving the bone screw into the subject's bone.

15. A receiving assembly for a bone screw comprising:
a receiver configured to be movably mounted on a head of the bone screw, the receiver defining a channel for receiving a rod member therein; and
a continuous retaining ring disposed within the receiver for holding the head of the bone screw in the receiver, the continuous retaining ring being configured to expand a receiving area of the retaining ring to permit at least a portion of the head of the bone screw to be inserted through the retaining ring;

wherein the retaining ring defines a plurality of channels, the receiving assembly further comprising a plurality of balls received in respective channels, the balls being moveable in the channels to expand the receiving area of the retaining ring.

* * * * *